United States Patent
Rivera

(10) Patent No.: US 7,495,454 B2
(45) Date of Patent: Feb. 24, 2009

(54) DEVICE FOR MEASUREMENT OF ELECTRICAL PROPERTIES IN MATERIALS

(75) Inventor: David F. Rivera, Westerly, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 254 days.

(21) Appl. No.: 11/706,683

(22) Filed: Feb. 12, 2007

(65) Prior Publication Data

US 2008/0191711 A1 Aug. 14, 2008

(51) Int. Cl.
*G01R 27/32* (2006.01)
*G01R 35/00* (2006.01)

(52) U.S. Cl. .................. 324/638; 324/642; 324/601

(58) Field of Classification Search .......... 324/601, 324/637–646
See application file for complete search history.

(56) References Cited

U.S. PATENT DOCUMENTS

| | | | |
|---|---|---|---|
| 4,247,815 A | 1/1981 | Larsen et al. | |
| 4,866,371 A * | 9/1989 | De | 324/639 |
| 5,187,443 A * | 2/1993 | Bereskin | 324/642 |
| 5,371,468 A | 12/1994 | Pelster | |
| 5,625,293 A | 4/1997 | Marrelli et al. | |
| 6,106,563 A | 8/2000 | Stengel et al. | |
| 6,147,502 A | 11/2000 | Fryer et al. | |
| 6,472,885 B1 | 10/2002 | Green et al. | |
| 6,856,140 B2 * | 2/2005 | Talanov et al. | 324/638 |
| 7,075,314 B2 * | 7/2006 | Ehata | 324/639 |
| 2005/0150278 A1 * | 7/2005 | Troxler et al. | 73/78 |

* cited by examiner

*Primary Examiner*—Timothy J Dole
(74) *Attorney, Agent, or Firm*—James M. Kasischke; Michael P. Stanley; Jean-Paul A. Nasser

(57) ABSTRACT

A device for measuring electrical properties, including permittivity, of a material is disclosed. The device includes a first conduit and second conduit terminating at open ends and respectively connected to a first and second connector port. Annuli are formed by the open ends to encompass portions of a flange of the device. The flange as well the portions make firm contact with the material under test, permitting simultaneous measurements of the complex scattering parameters of the material when an electromagnetic field is transmitted through the first connector port. Electrical characteristics of the material can be computed using the measurements received at the first connector port and the second connector port. Shorting screws are used for calibration by selectively opening or shorting the conduits.

6 Claims, 12 Drawing Sheets

DEVICE FOR MEASUREMENT OF ELECTRICAL PROPERTIES IN MATERIALS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates to a device used for measuring the permittivity of insulating materials over a broad range of frequencies.

(2) Description of the Prior Art

The electrical property of an insulator is an important piece of information that gives the designer the ability to choose the most appropriate material for a given application of the numerous electric characteristics that describe a given insulator, the relative permittivity (Symbol: $\in_r$) receives attention because the relative permittivity describes an insulator's ability to store and/or dissipate electric field energy. This is symbolized by writing $\in_r$, explicitly as the complex quantity.

$$\in_r = \in_r' - j\in_r'' \quad (1)$$

In the above, $\in_r'$ is called the dielectric constant and $\in_r''$ is the loss factor, both quantities varying with applied frequency. The symbol j indicates that there is a (90°) phase lag between $\in_r''$ and $\in_r'$. In a good dielectric, $\in_r'$ is much larger than $\in_r''$; the converse is true for a highly dissipative (lossy) insulator. Thus materials with loss factors large compared to the dielectric constant exhibit a temperature rise when exposed to intense field or high frequencies.

In certain applications, the magnetic properties of a material are required. For example: the magnetic properties of radar absorbing material (RAM). In this case, the relative permeability (Symbol $\mu_r$) must be known for the absorption capability of the RAM.

The permeability of a material is also a complex quantity and is written in the same way, that is, $$\mu_r = \mu_r' - j\mu_r'' \quad (2)$$

as it analogously describes the manner in which the material interacts with magnetic fields.

As described above, there exists a need for a device for measuring the permittivity and leading to a future method for measuring the permeability of either dielectric or magnetic materials or composites thereof over a wide band of frequencies. The important feature of the device is that it be nondestructive, so that the material to be tested does not require machining to any particular shape as required with other methods. Only a smooth flat surface is required for the device.

SUMMARY OF THE INVENTION

Accordingly, it is a general purpose and object of the present invention to provide a device for measuring the permittivity of either dielectric or magnetic materials or composites over a wide band of frequencies.

It is a further object of the present invention to provide a measuring device that does not require the material to be tested to be machined to any particular shape.

It is a still further object of the present invention to provide a measuring device only requires a smooth flat surface for operation.

In order to attain the objects described above, a measurement device is disclosed. The device is preferably constructed of Navy brass and can be made in different sizes scalable to alternate surfaces of a material under test.

The device utilizes two transmission line conduits that each terminate to open ends. Annuli formed by the open ends each encompass portions of a flange. The flange as well the portions makes firm contact with the material under test (MUT). When an electromagnetic field is launched from a connector port and propagates along the interior of one of the transmission line conduits to an open end and partially to the other conduit, simultaneous measurements of the complex scattering (or S) parameters $s_{11}$ and $s_{21}$ (which describe reflection and transmission, respectively) are gatherable. The scattering parameter $s_{11}$ for reflection is gatherable at the launching or loading connector port, whereas the scattering parameter $s_{21}$ is gatherable by being transmitted to the other connector port. From the measurements, the characteristics of the material in question can be computed by either a network analyzer or any other analyzer familiar to those skilled in the art.

The amount of field reflection and transmission depends on the electrical properties of the material under test and frequency, which is to say that factors such as capacitance are modified by the presence of the material under test relative to the absence of a material where the electromagnetic field is exposed to air.

Alternative devices would have different open end shapes and spacing for improved coupling and sensitivity. Size adjustment of the open ends for higher or lower frequency ranges is practicable. Also, improvements to the experimental models achievable with the device are possible with more elaborate networks that include the addition of components such as coils and resisters, to be represented in the model.

Shorting screws of the device are retractable for selectively opening or shorting the conduits for calibrating the device. The device is visually calibrated by shorting the transmission line conduits in conjunction with a Smith Chart which is electronically calculable as part of a network analyzer.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals and symbols designate identical or corresponding parts throughout the several views and wherein.

DETAILED DESCRIPTION OF THE INVENTION

Figure 1:
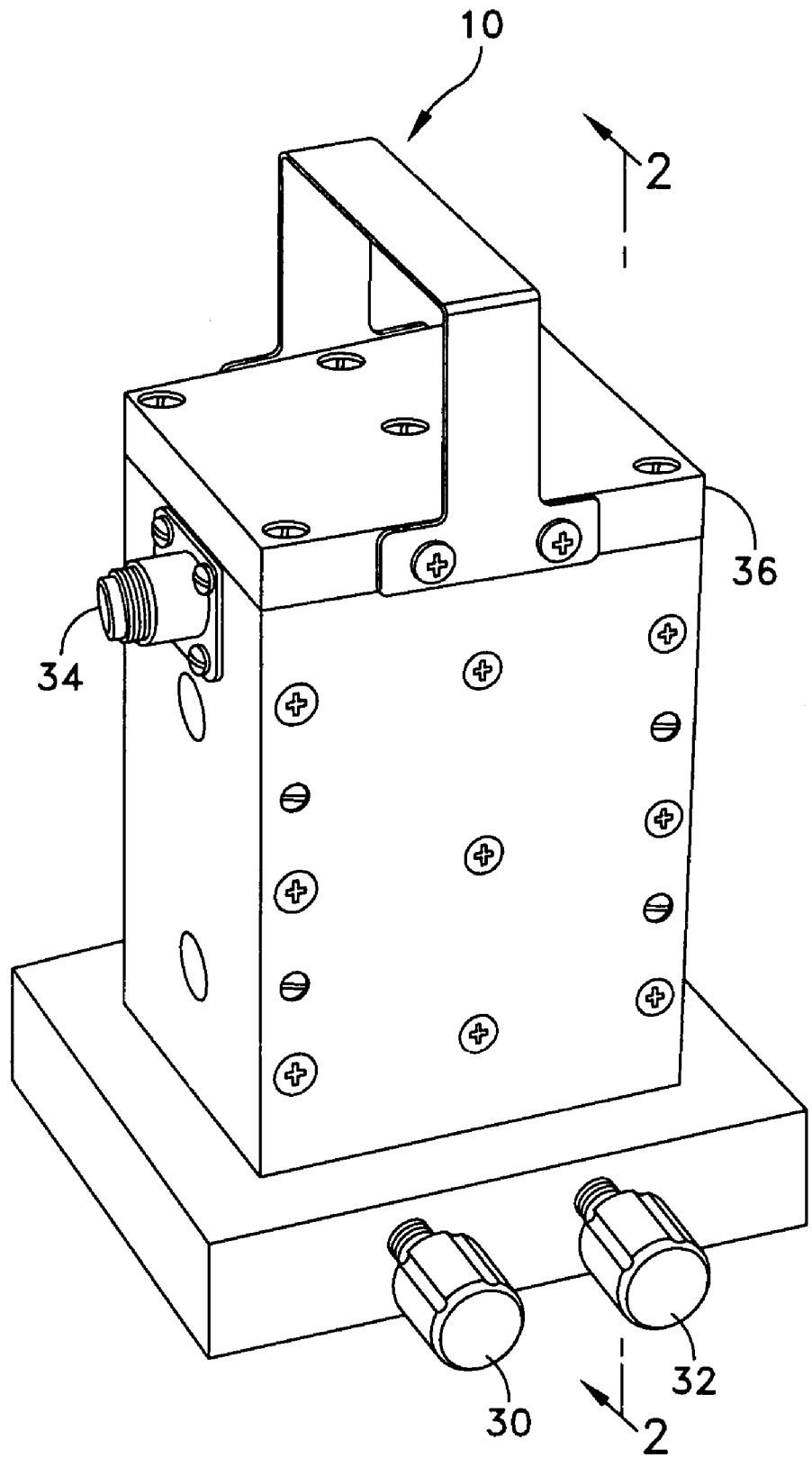
FIG. 1 is an isometric view of the device of the present invention.
Figure 2:
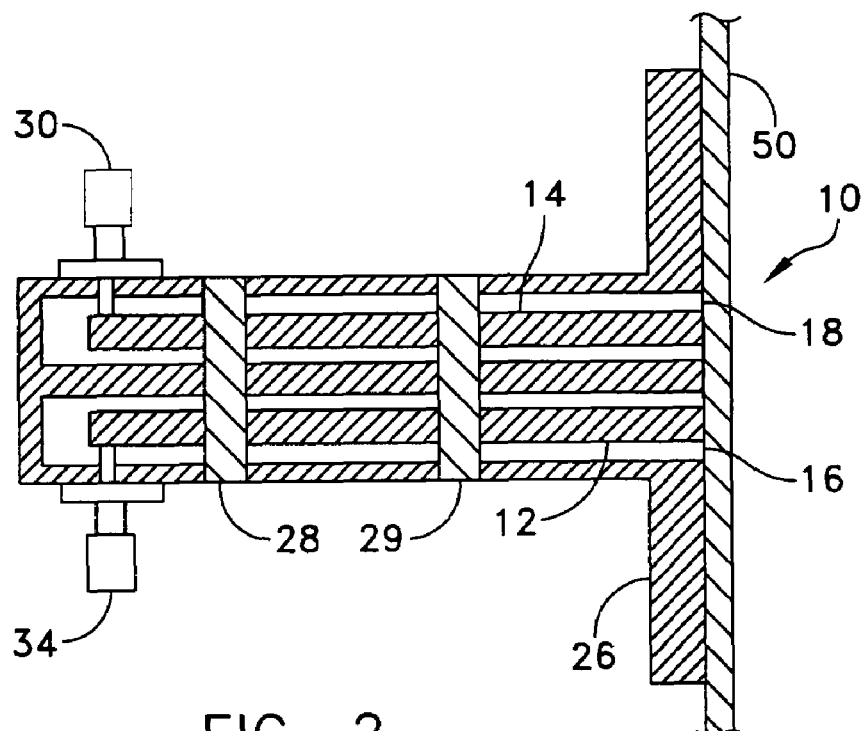
FIG. 2 is a cross-sectional view of the device of the present invention with the view taken from reference line 2-2 of FIG. 1.
Figure 3:
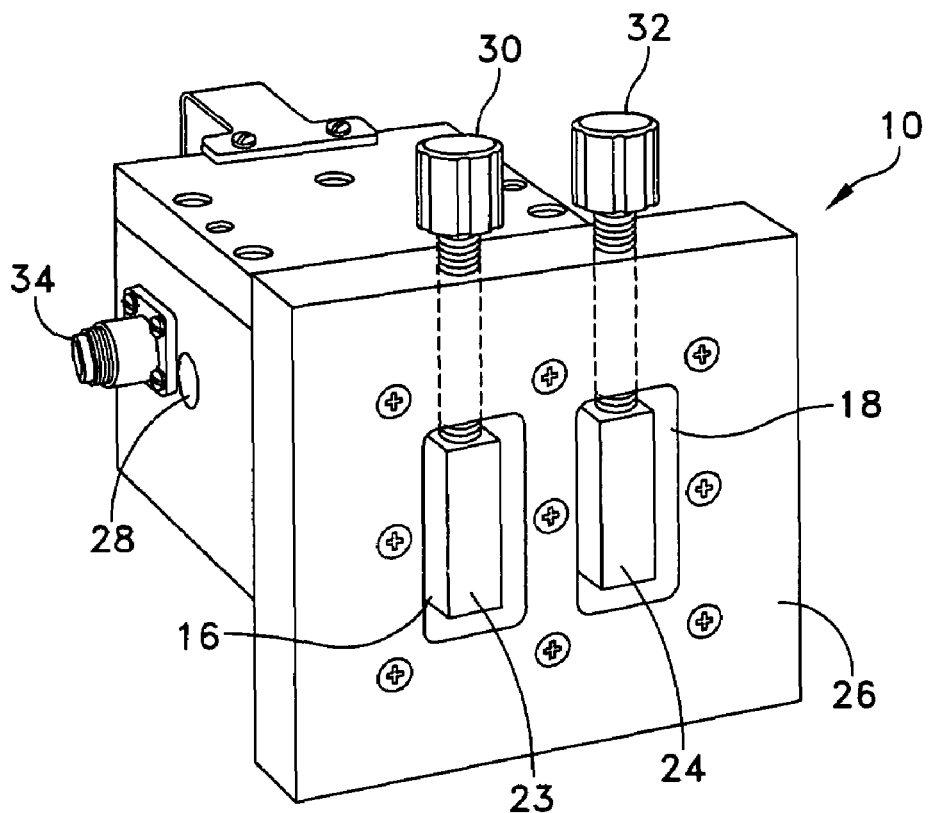
FIG. 3 is an alternative isometric view of the device of the present invention.

An exterior view of the measurement device 10 of the present invention is shown in FIG. 1 with a cross-sectional view shown in FIG. 2. An alternate exterior view is shown in FIG. 3. The measurement device 10 used in the example below is constructed of Navy brass and can be made in different sizes scalable to alternate surfaces of a material under test 50. Other suitable materials other than Navy brass and known to those skilled in the art may be used. For purposes of explanation of use, the following symbols are incorporated for the equations and explanation that follow:

j=Complex number (j=$\sqrt{-1}$);
$\epsilon_e'$=Effective dielectric constant in probe conduit ($\epsilon_e' \approx 1.4$);
$\epsilon_{s1}$=Complex permittivity of first calibration standard, relative to free space ($\epsilon_{s1}=\epsilon_{s1}'-j\epsilon_{s1}''$);
$\epsilon_{s2}$=Complex permittivity of second calibration standard relative to free space ($\epsilon_{s2}=\epsilon_{s2}'-j\epsilon_{s2}''$);
$\epsilon_M'$=Dielectric constant of unknown material under test, relative to free space
tan $\delta_M$=Loss tangent of unknown material under test
$\lambda_0$=Free space wavelength, meters;
$k_0$=Free space wave number ($k_0=2\pi/\lambda_0$), meter$^{-1}$;
$\gamma$= Complex propagation constant of probe conduit; ($\approx jk_0 \sqrt{\epsilon_e}$), meter$^{-1}$;
p=Mean perimeter of annular aperture (open end);
L=Length of probe conduit, meters;
$s_{11}$=Complex scattering (or s-) parameter, reflection;
$s_{21}$=Complex scattering (or s-) parameter, transmission;
$Y_a$=Admittance of isolated aperture, Siemens;
$Y_m$=Mutual admittance between aperture, Siemens;
$Z_a$=Impedance of isolated aperture on open ends, Ohms $Z_a=1/Y_a$;
$Z_m$=Mutual impedance between apertures on open ends, Ohms $Z_m=1/Y_m$;
$Z_c$=Characteristic impedance of probed conduit ($Z_c \approx 25$ Ohms);
$Z_o$=Characteristic impedance of the measurement system ($Z_o \approx 25$ Ohms); and
$\Delta Z$=Difference of the isolated aperture and mutual impedances, respectively: $\Delta Z=Z_a-Z_m$ Physically, the measurement device 10 utilizes two transmission line conduits 12 and 14 that each terminate to open ends 16 and 18. The open ends 16 and 18 each form annuli to encompass portions 23 and 24 of a flange 26. The portions 23 and 24 maintain their position within the device 10 with the use of plastic standoffs 28 and 29. With the portions 23 and 24 maintained in position, the conduits 12 and 14 remain dimensionally stable. In operation, the flange 26 as well the portions 23 and 24 make firm contact with the material under test (MUT) 50.

Figure 4:
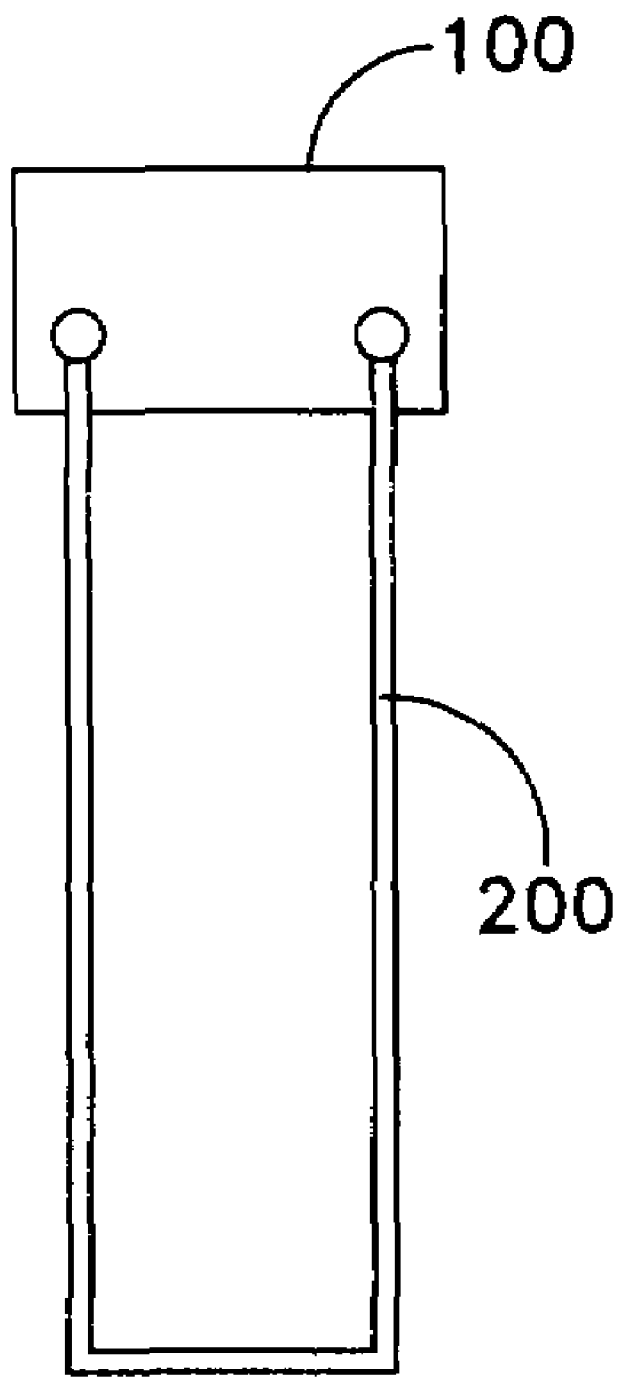
FIG. 4 is a schematic depicting an initial calibration setup for the device of the present invention.
Figure 5:
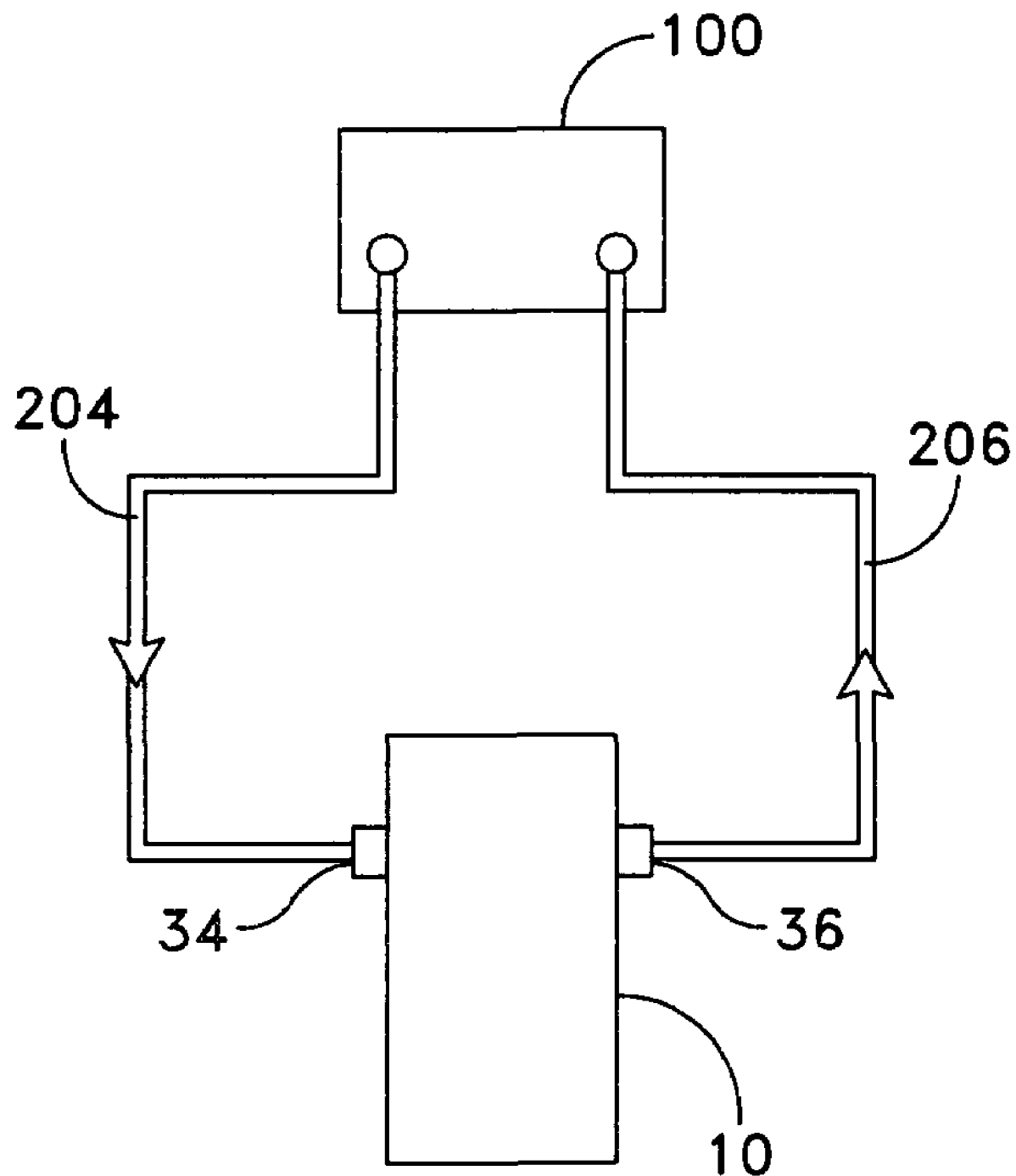
FIG. 5 is a schematic depicting a follow-on calibration setup from FIG. 4 for the device of the present invention.

The shorting screws 30 and 32 retract for selectively opening or shorting the two transmission line conduits 12 and 14 for calibration purposes. When calibrating, a network analyzer 100, shown diagrammatically in FIG. 4, tests the flow-thru impedance of a coaxial cable 200. The coaxial cable is segmented to sections 204 and 206 for attachment to connector ports 34 and 36 of the measurement device 10. The measurement device 10 is visually calibrated by shorting the transmission line conduits 12 and 14 in conjunction with a Smith Chart which is electronically calculable as part of the network analyzer 100 (See FIG. 5).

The shorting screws 30 and 32 also allow the length of the conduits 12 and 14 from the connector ports 34 and 36 to be short enough that the phase from the connector ports to the open ends 16 and 18 is invariant. If the shorting screws 30 and 32 were absent, the length of the conduits 12 and 14 would have to be accounted for.

In operation, simultaneous measurements of the complex scattering (or s-) parameters $s_{11}$ and $s_{21}$ (which describe reflection and transmission, respectively) are permitted from which the characteristics of the material under test 50 can be computed. The operation of the device is understood by referring to the general electrical equivalent circuit shown in FIG. 6. The circuit is a general equivalent in that the use of variable impedances allows construction of the device 10 at different scales.

Figure 6:
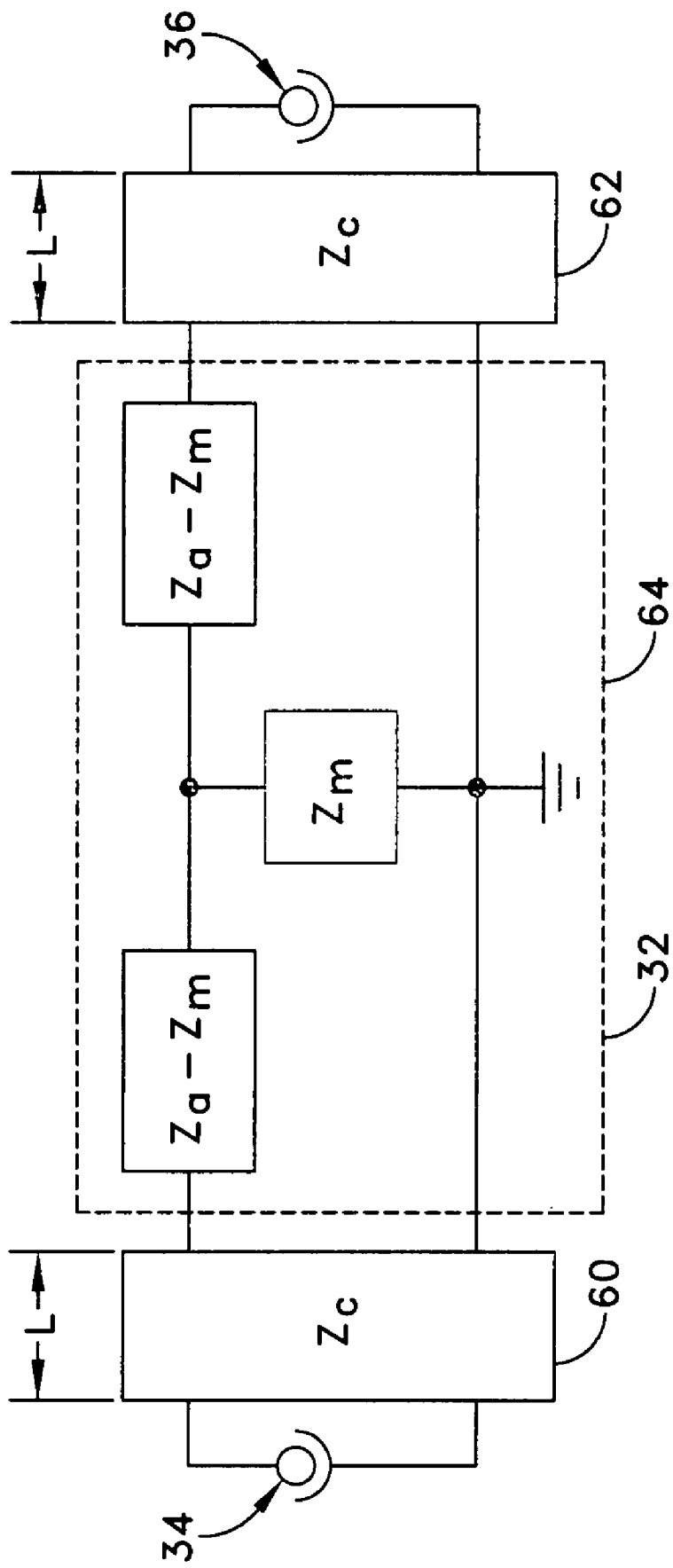
FIG. 6 is a diagram of the electrical equivalent circuit of the device of the present invention.

In the FIG. 6, the measurement device 10 reflects several elements. Rectangular boxes 60 and 62 respectively at connector ports 34 and 36 diagrammatically represent the transmission line conduits 12 and 14, each with characteristic impedance $Z_o$ and a physical length L that respectfully lead to the open ends 16 and 18, with the electromagnetic activity at the opens ends represented by a coupled-aperture circuit within dotted box 64. The coupled-aperture circuit is made up of three elements configured as a T-network with complex impedances $Z_a-Z_m$ and $Z_m$.

$Z_a$ is the impedance of an isolated open end (that is, with no neighbor, either the open end 16 or 18) and $Z_m$ is the mutual impedance between the open ends, this value depending on their proximity to each other.

When an electromagnetic field is loaded by the network analyzer 100, thru the co-axial cable section 204 and launched from port 34, the electromagnetic field propagates along the interior of the transmission line conduit 12, until the electromagnetic field reaches the open end 16. The discontinuity presented by the open end 16 causes the incident field (from the conduit 12) striking the material under test 50 to be partially reflected back into the conduit, accompanied by a (small) portion of the incident field that propagates from one open end 16 to the other open end 18, which is then guided by the other conduit 14 and measured at connector port 36. The measurement at the connector port 36 is monitored by the network analyzer 100. The electromagnetic field reflected back into the conduit 12 is measured at the connector port 34 and is also monitored by the network analyzer 100.

The amount of field reflection and transmission depends on the electrical properties of the material under test 50 and frequency, which is to say that the T-network shown in FIG. 6 is modified by the presence of the material under test relative to air.

Figure 7:
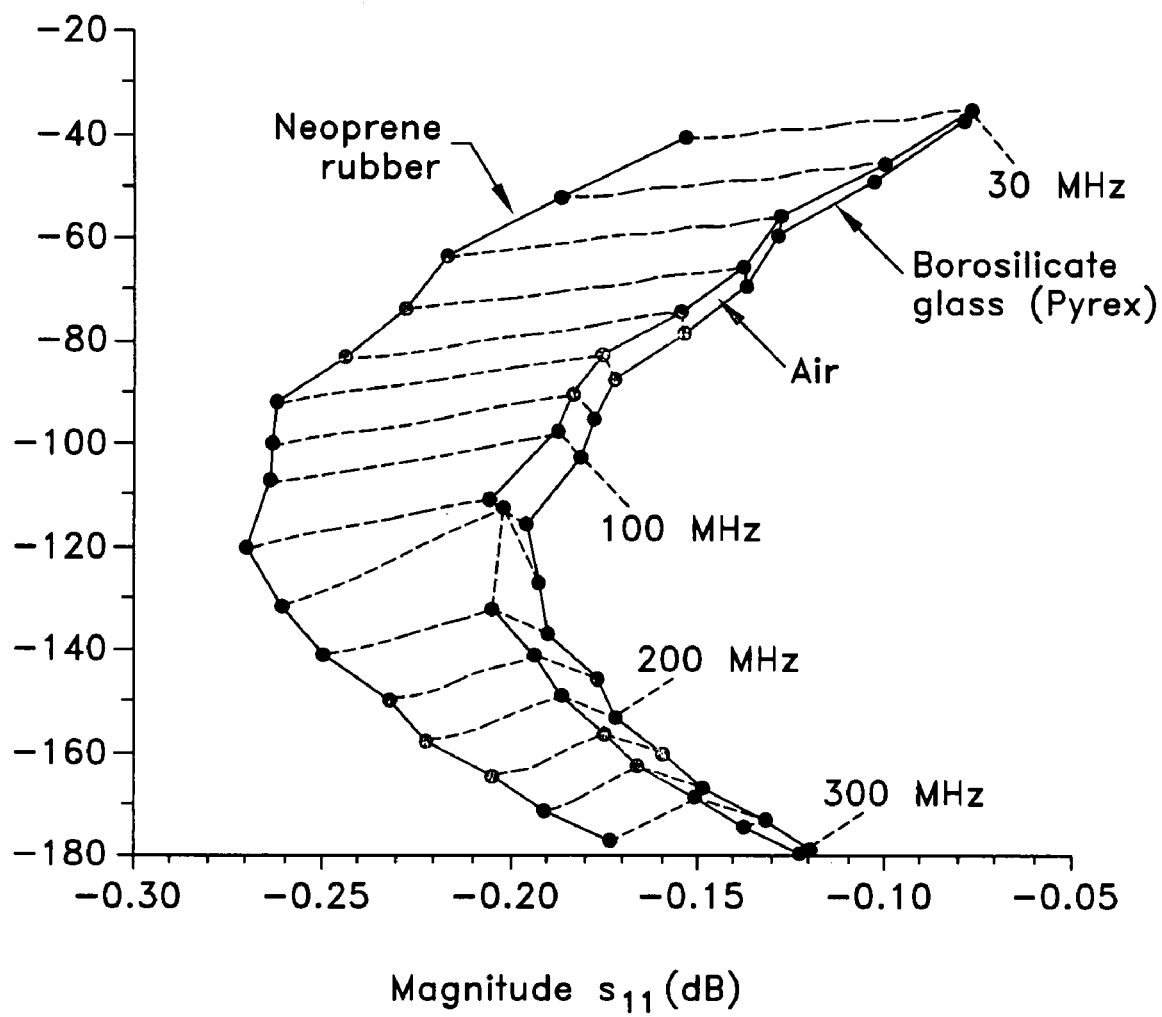
FIG. 7 is a chart of data giving the scattering parameter $s_{11}$ as a function of frequency and material type.
Figure 8:
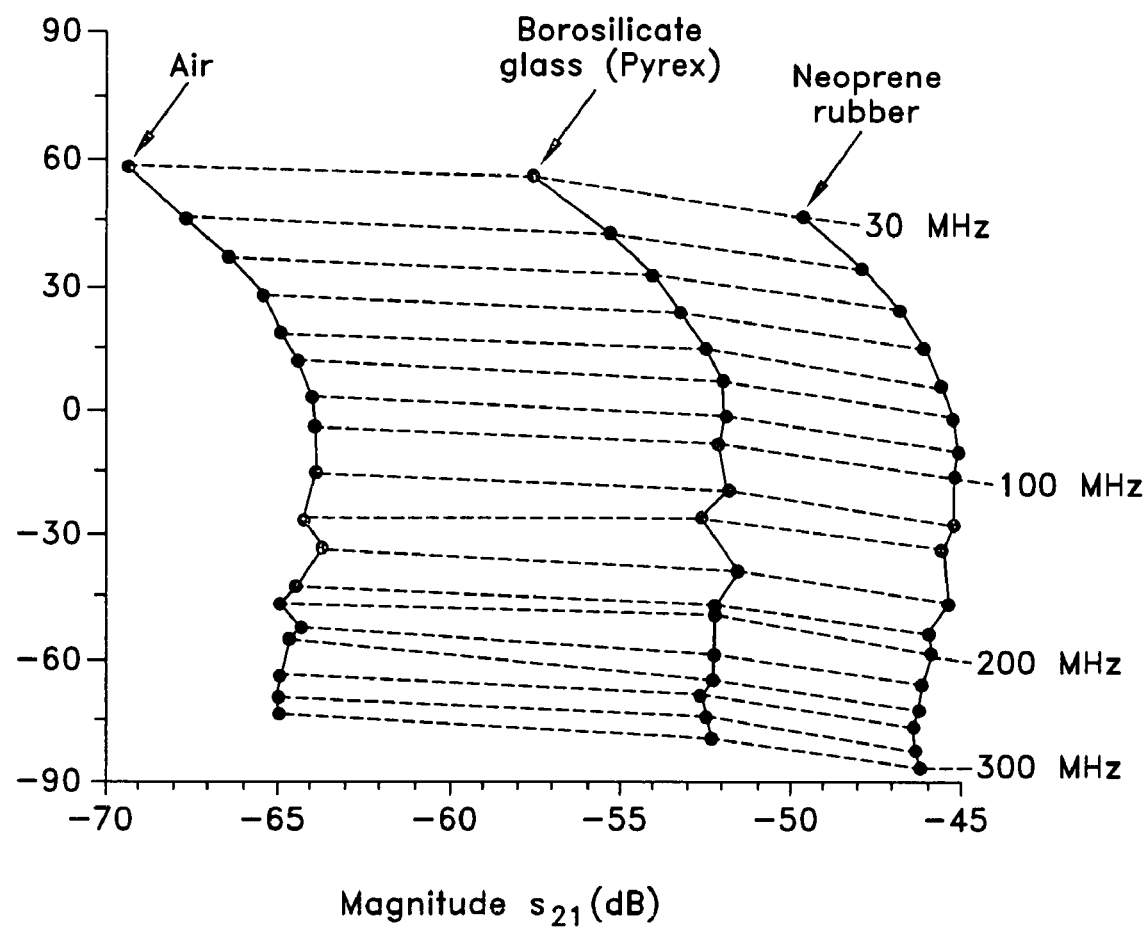
FIG. 8 is a chart of data giving the scattering parameter $s_{21}$ as a function of frequency and material type.

Experimental VHF data (30-300 MHz) giving the scattering parameters $s_{11}$ and $s_{21}$ as a function of frequency and material type are shown in FIGS. 7 and 8. The material permittivities in the measurements are:

Air: $\epsilon_r=1$
Borosilicate glass (Pyrex): $\epsilon_r=4.6-j0.023$
Neoprene rubber: $\epsilon_r=6-j0.55$ The values for Pyrex and Neoprene are 30 MHz and 300 MHz. The relative sizes of the permittivities translate to measurable shifts in both the amplitude and phase of $s_{11}$ and $s_{21}$.

The measurements shown in FIGS. 7 and 8 are useful because the measurements illustrate the manner in which various materials incur translational and/or rotational shifts in $s_{11}$ (FIG. 7) and $s_{21}$ (FIG. 8).

Figure 9:
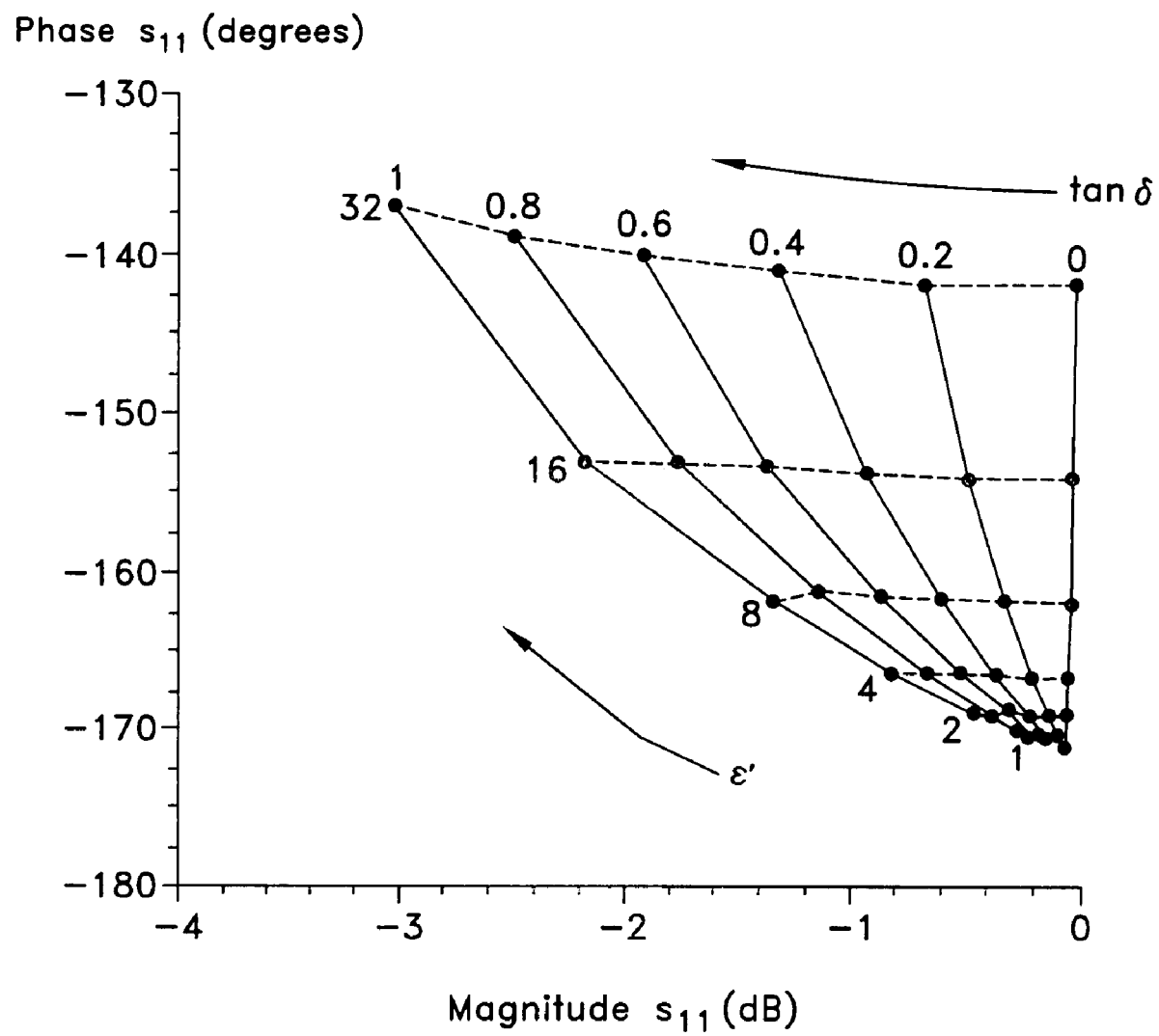
FIG. 9 is a chart correlating an arbitrary value of $\epsilon_r$ to a corresponding value of $s_{11}$ with a frequency in the figure held constant at 300 MHz.
Figure 10:
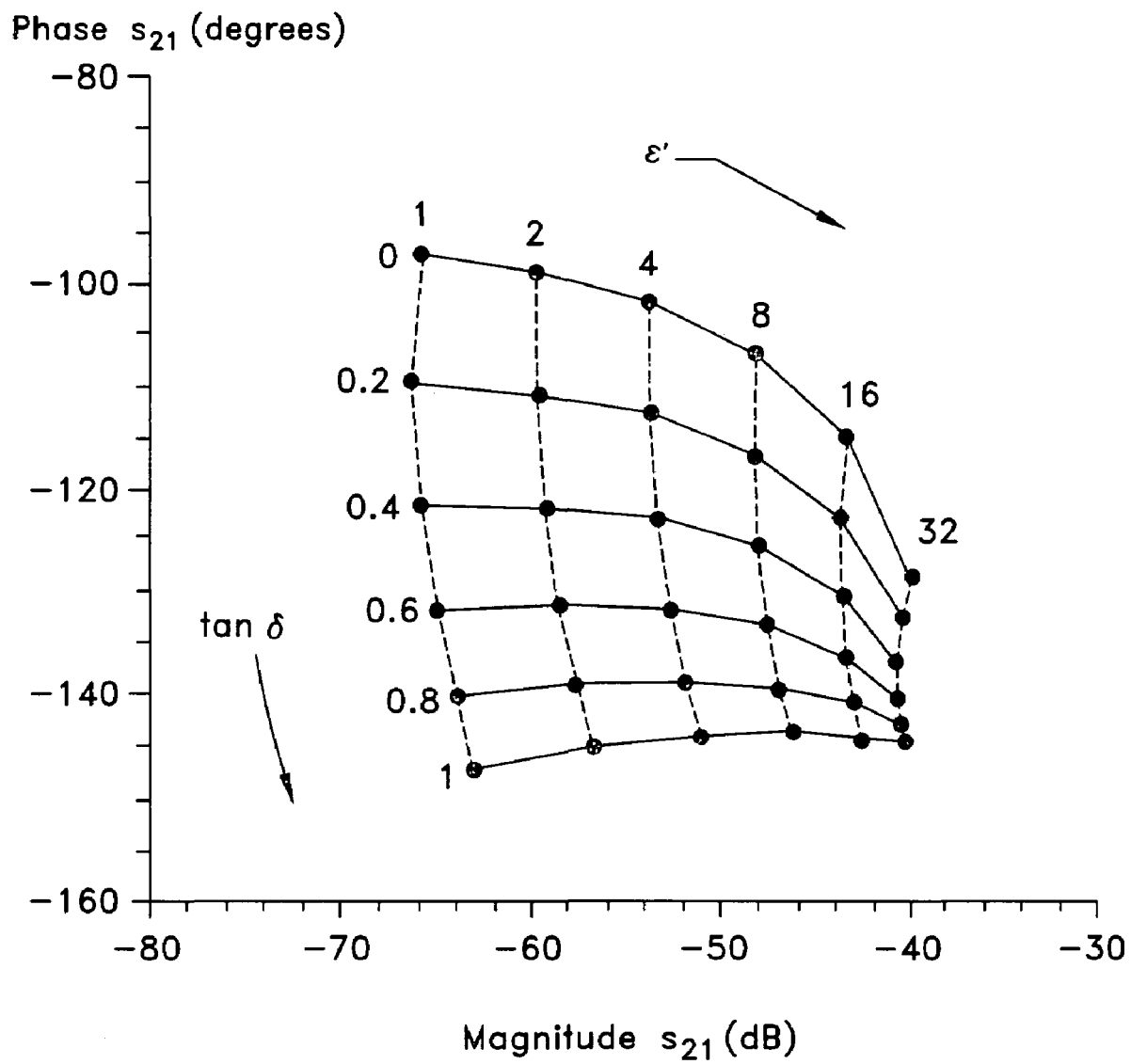
FIG. 10 is a chart correlating an arbitrary value of $\epsilon_r$ to a corresponding value of $s_{21}$ with a frequency in the figure held constant at 300 MHz.

The utility of the measurement device 10 is additionally shown by employing charts that correlate or "map" an arbitrary value of $\in_r$ to a corresponding value of $s_{11}$ (See FIG. 9) or $s_{21}$. (See FIG. 10). In the figures, the frequency is held constant at 300 MHz. Thus, by measuring $s_{11}$ and $s_{21}$ at a given frequency, reference to the charts will yield the value of $\in_r$. Other charts can be prepared for other frequencies and material types.

Derivation

To support the operation of the device 10, further explanation is provided as to how electrical measurements are derived. For admittance of the isolated and mutual conduits 12 and 14, the determination of admittances $Y_a$ and $Y_m$ in terms of s–parameters $s_{11}$ and $s_{21}$ begin with some properties of the device 10. Presented at the outset are simplified calculations: The physical dimensions of the probe apertures at the open ends 16 and 18 of the device 10 are small compared to the wave length at the highest frequency of operation; the electromagnetic coupling between connector ports 34 and 36 is due to the presence of the quasi-static fields within which energy is stored and not to radiation; and the probe apertures at the open ends 16 and 18 are identical in both shape and size.

Figure 11:
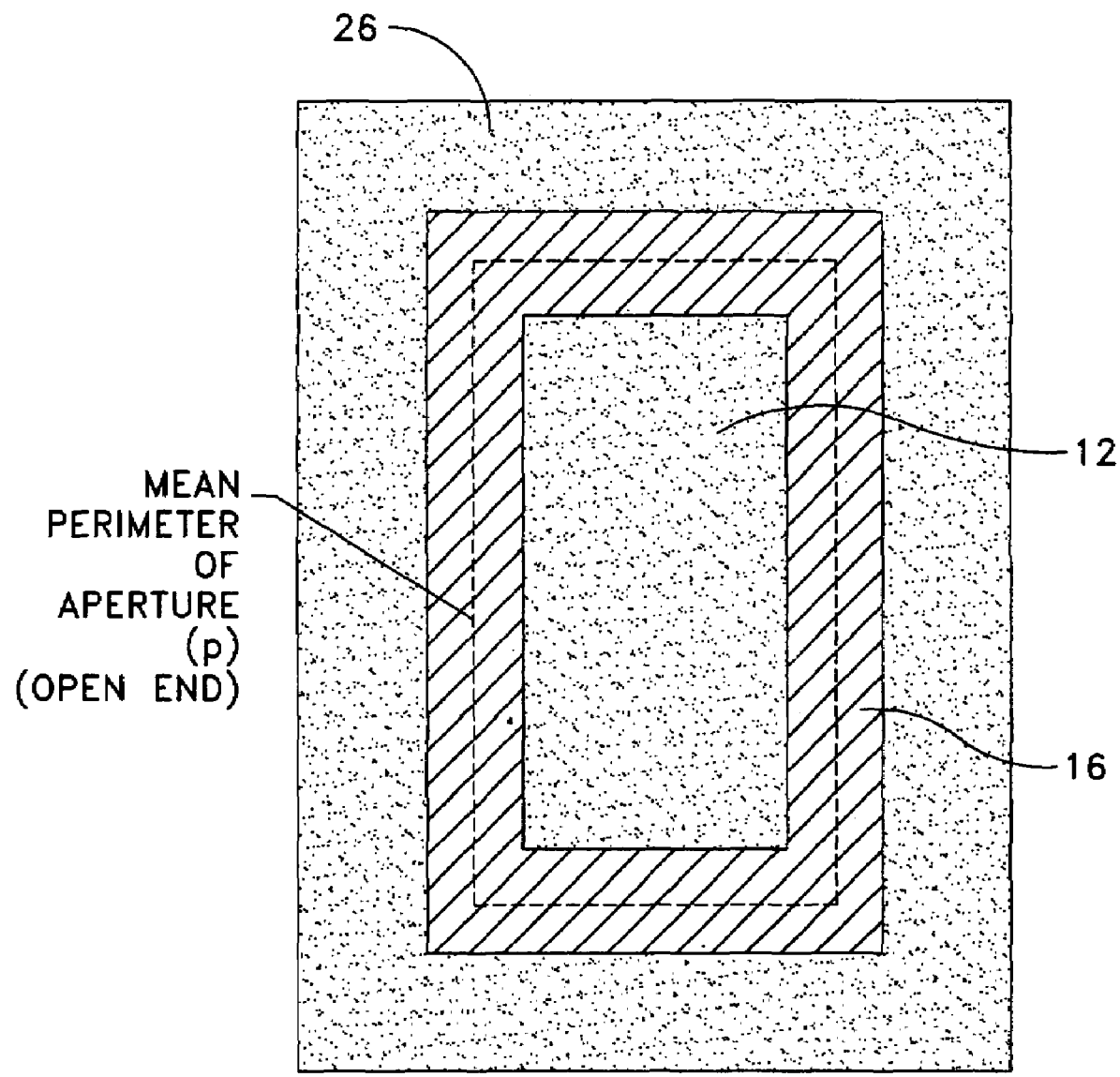
FIG. 11 is a view depicting the flange of the device of the present invention.

The first assumption is depicted in FIG. 11. In the figure, a close up of the annular conduit with open end (shown here as being rectangular but could be arbitrary shaped from the conduit 12) is shown. The aperture 12 of the conduit is said to be electrically small when the mean perimeter (p) is smaller than the smallest wavelength (i.e., the wave length at the highest frequency), or $$\frac{P}{\lambda} \ll 1. \tag{3}$$

The second assumption follows from the first. When the perimeter is electrically small, losses due to radiation are neglected, greatly reducing the complexity of the electromagnetic analysis. The third condition yields a device, which is symmetrical with regard to power transfer between ports.

The third assumptions outlined now permit an analysis of the device 10 as a two-port network to yield the required admittances.

Figure 12:
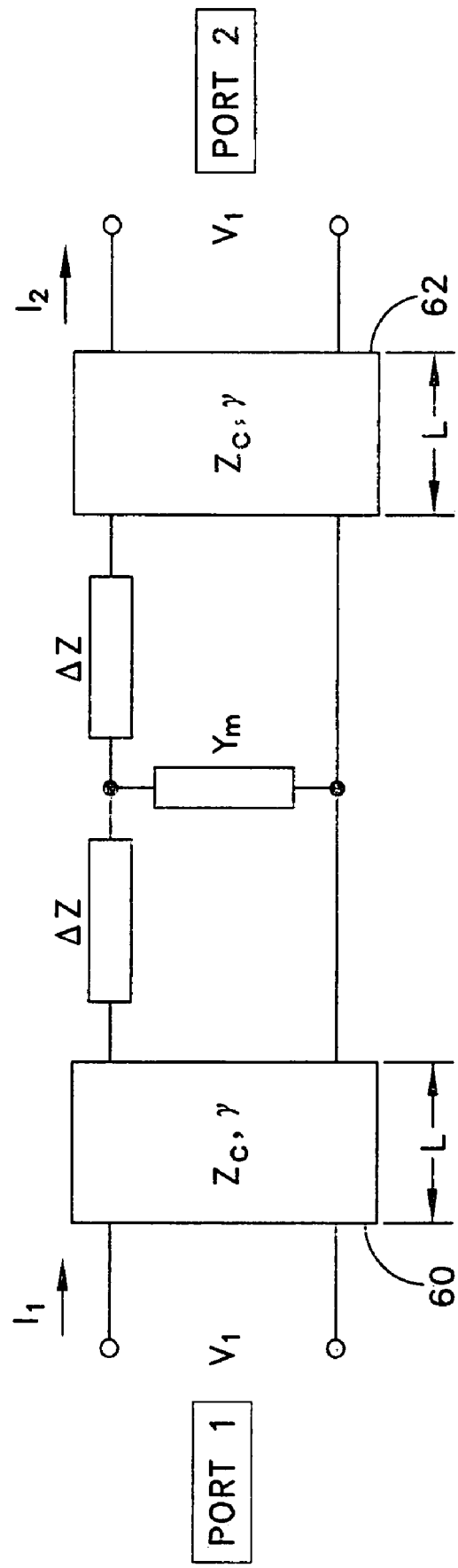
FIG. 12 is a diagram of an alternate electrical equivalent circuit of the device of the present invention.

In FIG. 12, the large rectangular boxes represent the coaxial transmission line conduits 12 and 14, each having a characteristic impedance of value $Z_c$ and complex propagation constant $\gamma$. The small and remaining boxes represent the electrical elements, which describe the interaction between the fields and the material under test (MUT). The impedance element $\Delta Z$ thus describes the interaction of the aperture of one conduit 60 with the MUT while in the presence of the aperture of the other conduit 62. The admittance element $Y_m$, on the other hands, is a measure of the degree of electromagnetic coupling between the two conduits in the presence of the MUT.

The voltage and current ($V_1$, $I_1$) at Port 1 are related to the corresponding quantities at Port 2 ($V_2$, $I_2$) through the relationship $$V_1 = AV_2 + BI_2$$

$$I_1 = CV_2 + DI_2 \tag{4}$$

and rewritten in matrix form as $$\begin{pmatrix} V_1 \\ I_1 \end{pmatrix} = \begin{pmatrix} A & B \\ C & D \end{pmatrix} \begin{pmatrix} V_2 \\ I_2 \end{pmatrix} \tag{5}$$

where elements A, B, C and D are defined as follows:

A is a voltage ratio when Port 2 is open circuited ($A=V_1/V_2$ when $I_2=0$);

B is the transfer impedance when Port 2 is short-circuited ($B=V_1/I_2$ when $V_2=0$)

C is the transfer admittance when Port 2 is open circuited ($C=I_1/I_2$ when $I_2=0$); and D is a current ratio when Port 2 is short-circuited ($D=I_1/I_2$ when $V_2=0$)

The total ABCD matrix of the device 10 is matter of multiplying the ABCD matrices of each element comprising the device, starting from Port 2 and working toward Port 1:

$$\begin{pmatrix} A & B \\ C & D \end{pmatrix} = \begin{pmatrix} \cosh \gamma L & Z_c \sinh \gamma L \\ \frac{\sinh \gamma L}{Z_c} & \cosh \gamma L \end{pmatrix} \begin{pmatrix} 1 & \Delta Z \\ 0 & 1 \end{pmatrix} \begin{pmatrix} 1 & 0 \\ Y_m & 1 \end{pmatrix} \begin{pmatrix} 1 & \Delta Z \\ 0 & 1 \end{pmatrix} \tag{6}$$

$$\begin{pmatrix} \cosh \gamma L & Z_c \sinh \gamma L \\ \frac{\sinh \gamma L}{Z_c} & \cosh \gamma L \end{pmatrix} = \begin{pmatrix} \cosh \gamma L & Z_c \sinh \gamma L \\ \frac{\sinh \gamma L}{Z_c} & \cosh \gamma L \end{pmatrix}$$

$$\begin{pmatrix} 1 + \Delta Z Y_m & \Delta Z(2 + \Delta Z Y_m) \\ Y_m & 1 + \Delta Z Y_m \end{pmatrix} \begin{pmatrix} \cosh \gamma L & Z_c \sinh \gamma L \\ \frac{\sinh \gamma L}{Z_c} & \cosh \gamma L \end{pmatrix}$$

where the probe is modeled as a bilateral network in which $s_{11}=s_{22}$ and $s_{12}=s_{21}$, and:

$$A = \frac{1 - s_{11}^2 + s_{21}^2}{2s_{21}} \tag{7}$$

$$B = Z_o \left[ \frac{(1+s_{11})^2 - s_{21}^2}{2s_{21}} \right]$$

$$C = \frac{1}{Z_o} \left[ \frac{(1-s_{11})^2 - s_{21}^2}{2s_{21}} \right]$$

$$D = A$$

The admittances $Y_a$ and $Y_m$ are expressed in terms of the scattering parameters $s_{11}$ and $s_{21}$ by substituting $$\begin{pmatrix} 1 + \Delta Z Y_m & \Delta Z(2 + \Delta Z Y_m) \\ Y_m & 1 + \Delta Z Y_m \end{pmatrix} = \begin{pmatrix} \frac{Y_m}{Y_a} & \left(\frac{Y_m}{Y_a} - \frac{1}{Y_m}\right) \\ Y_m & \frac{Y_m}{Y_a} \end{pmatrix} \tag{8}$$

and solving the matrix equation $$\begin{pmatrix} \frac{Y_m}{Y_a} & \left(\frac{Y_m}{Y_a^2} - \frac{1}{Y_m}\right) \\ Y_m & \frac{Y_m}{Y_a} \end{pmatrix} = \tag{9}$$

-continued $$\begin{pmatrix} \cosh \gamma L & Z_c \sinh \lambda L \\ \frac{\sinh \lambda L}{Z_c} & \cosh \gamma L \end{pmatrix}^{-1} \begin{pmatrix} A & B \\ C & D \end{pmatrix} \begin{pmatrix} \cosh \gamma L & Z_c \sinh \lambda L \\ \frac{\sinh \lambda L}{Z_c} & \cosh \gamma L \end{pmatrix}^{-1}$$

Yielding admittances $Y_a$ and $Y_m$ are given explicitly by:

$$Y_a = \frac{1}{Z_c}\left[\frac{1+\cosh 2\gamma L - k_1(1+k_2\sinh 2\gamma L)}{k_1 k_2 \cosh 2\gamma L - \sinh \gamma L}\right] \quad (10)$$

$$Y_m = \frac{1}{Z_o}\left(\frac{k_3}{k_1}\right)[1+\cosh 2\gamma L - k_1(1+k_2\sinh 2\gamma L)]$$

where $$k_1 = \frac{2}{1+\left(\frac{Z_c}{Z_o}\right)^2\left[\frac{(1-s_{11})^2-s_{21}^2}{(1+s_{11})^2-s_{21}^2}\right]} \quad (11)$$

$$k_2 = \left(\frac{Z_c}{Z_o}\right)\left[\frac{1-s_{11}^2+s_{21}^2}{(1+s_{11})^2-s_{21}^2}\right]$$

$$k_3 = \frac{(1-s_{11})^2-s_{21}^2}{2s_{21}}$$

For the permittivity of MUT, the dielectric properties of the MUT are determined with the aid of admittances $Y_a$ and $Y_m$ defined in equation (10). The remaining relationships which link the admittances with the dielectric properties of the MUT and frequency are now discussed.

The mutual or isolated admittance of the coaxial aperture at the open end 16 (or any aperture in general similar to the open end) is theoretically determined by utilizing a two-dimensional Fourier transform over the spectrum of plane waves radiated by or between apertures. This process is cumbersome for even the simplest aperture geometries. The admittances at low frequencies have simple algebraic forms of the type:

$$Y_a \approx j(a_1 k + a_3 k^3)\sqrt{\epsilon_r}$$

$$Y_m \approx -j[b_1 k' + b_3(k')^3]\sqrt{\epsilon_r} \quad (12)$$

where $$k = k_o\sqrt{\epsilon_r}$$

$$k' = k_o\sqrt{\epsilon_r'} \quad (13)$$

In equations (12) and (13), coefficients $a_n$ and $b_n$ (n=1, 3) are complex and frequency dependent. Moreover, the coefficients account for the aperture shape and their separation.

The permittivity of the unknown dielectric $\epsilon_M$ is then determined in the following way:

1. Using a first dielectric standard (with value $\epsilon_r = \epsilon_{s1}$, measure $s_{11}$ and $s_{21}$ as a function of frequency and save; the self and mutual admittances from this measurement, denoted as $Y_a^{s1}$ and $Y_m^{s2}$ are determined by Equation (11).
2. Using a second dielectric standard (with value $\epsilon_r = \epsilon_{s2}$), measure $s_{11}$ and $s_{21}$ as a function of frequency and save; the self and mutual admittances from this measurement, denoted as $Y_a^{s2}$ and $Y_m^{s2}$ are determined by equation (11).
3. Using the admittances determined by Equation (11), compute the admittance coefficients $a_1$, $a_3$, $b_1$, $b_3$ in Equations (12) and (13) by $$a_1 = \frac{1}{k_0(\epsilon_{s2}-\epsilon_{s1})}\left[\left(\frac{\epsilon_{s2}}{\epsilon_{s1}}\right)Y_a^{s1}-\left(\frac{\epsilon_{s1}}{\epsilon_{s2}}\right)Y_a^{s2}\right] \quad (14)$$

$$a_3 = -\frac{1}{k_o^3(\epsilon_{s2}-\epsilon_{s1})}\left[\frac{Y_a^{s1}}{\epsilon_{s1}}-\frac{Y_a^{s2}}{\epsilon_{s2}}\right] \quad (15)$$

$$b_1 = -\frac{1}{k_o(\epsilon_{s2}'-\epsilon_{s1}')}\left[\frac{Y_m^{s1}}{\sqrt{1-j\tan\delta_{s1}}}\left(\frac{\epsilon_{s2}'}{\epsilon_{s1}'}\right)-\frac{Y_m^{s2}}{\sqrt{1-j\tan\delta_{s2}}}\left(\frac{\epsilon_{s1}'}{\epsilon_{s2}'}\right)\right] \quad (16)$$

$$b_3 = \frac{1}{k_0^3(\epsilon_{s2}'-\epsilon_{s1}')}\left[\frac{Y_m^{s1}}{\epsilon_{s1}'\sqrt{1-j\tan\delta_{s1}}}-\frac{Y_m^{s2}}{\epsilon_{s2}'\sqrt{1-j\tan\delta_{s2}}}\right] \quad (17)$$

The dielectric constant $\epsilon_M'$ and loss tangent $\tan\delta_M$ of the MUT is initially determined by assuming that the measurement frequency is low enough so that the admittances in Equations (12) and (13) are linear functions of frequency, or $$Y_a \approx j a_1 k \sqrt{\epsilon_M} \quad (18)$$

$$Y_m \approx -j b_1 k' \sqrt{\epsilon_M} \quad (19)$$

where the complex coefficients $a_1$ and $b_1$ are computed using Equations (16) and (17). The dielectric constant and loss tangent of the MUT is then found initially by $$\epsilon_M' \approx \frac{a_1}{jk_o Y_a^M}\left(\frac{Y_m^M}{b_1}\right)^2 \quad (20)$$

$$\tan\delta_M \approx j\left[\left(\frac{b_1 Y_a^M}{a_1 Y_m^M}\right)^2 - 1\right] \quad (21)$$

Figure 13:
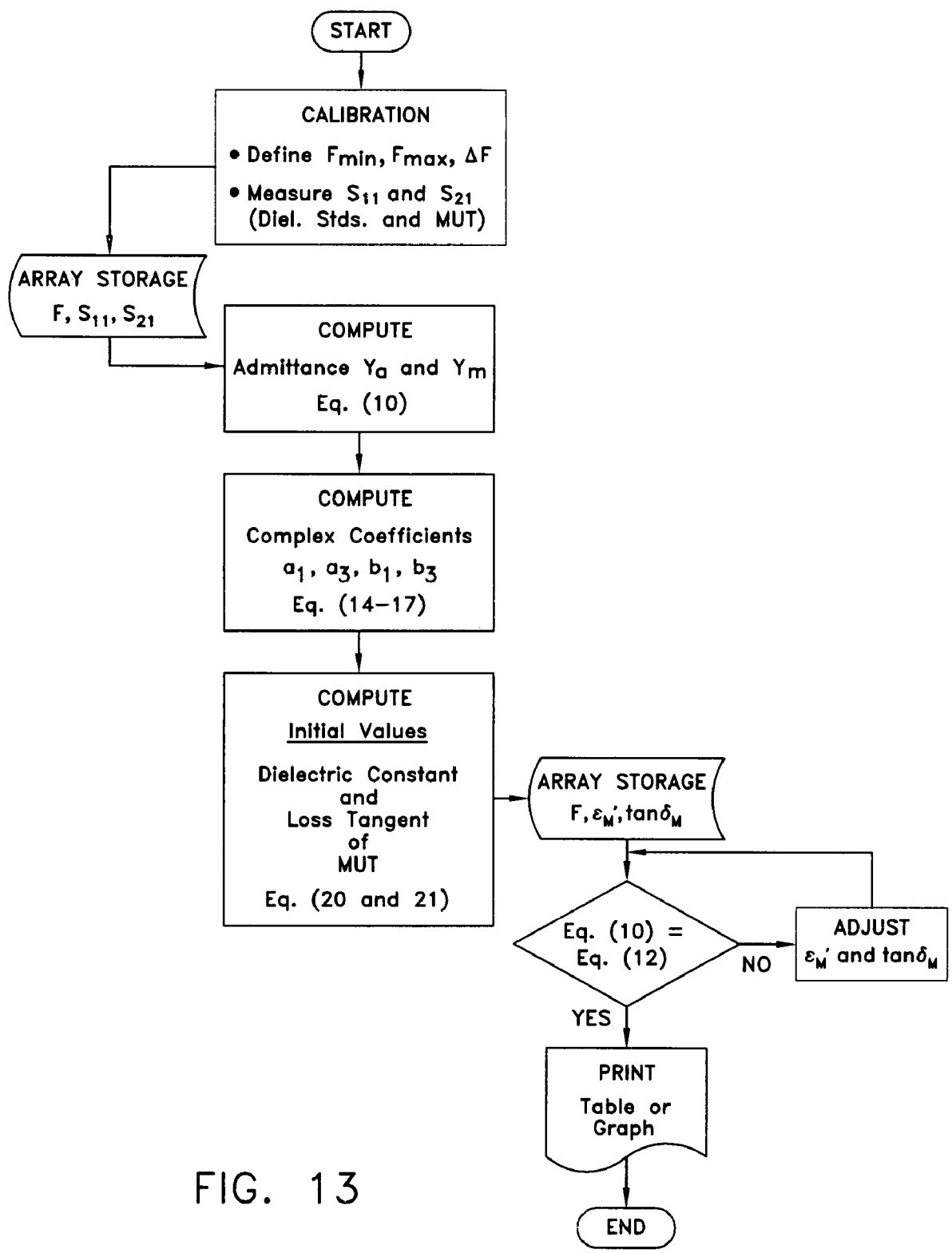
FIG. 13 is a flowchart for determining $\epsilon_M$ by utilizing calibration standards and measured s-parameters.

A refinement in the permittivity of the MUT can be obtained by substituting the initial values given in Equations (20) and (21) followed by numerical adjustment until the admittances given by Equation (11) agree with those computed using Equations (12) and (13). This last step can be performed with the aid of a complex root-finding technique, such as Müller's method. The flowchart in FIG. 13 outlines the steps required to find the relative permittivity of the MUT.

Alternative devices would have different open end shapes and spacing for improved coupling and sensitivity. Size adjustment of the open ends 16 and 18 for higher or lower frequency ranges is practicable. Also, improvements to the experimental models achievable with the device 10 are possible with more elaborate networks that include the addition of components such as coils and resisters, to be represented in the model.

While the invention has been described in connection with what is considered to be the most practical and preferred embodiment, it should be understood that this invention is not to be limited to the disclosed embodiment, but on the contrary, is intended to cover various modifications and equivalent arrangements included within the spirit and scope of the appended claims.

What is claimed is:

1. A device for measuring electrical properties of a material, said device comprising:
   a body;
   a first connector port positioned on an exterior of said body, said first connector port connectable to a first cable of an analyzer;
   a second connector port positioned on the exterior of said body, said second connector port connectable to a second cable of the analyzer;

a flange positioned on said body at an end opposite to the positioning of said first and second connector ports;

a first conduit connected to said first connector port, said first conduit terminating at an open end to form a first annulus encompassing a portion of said flange; and a second conduit connected to said second connector port, said second conduit terminating at an open end to form a second annulus encompassing a portion of said flange;

wherein said encompassed portions of said annuli as well as said flange are contactable with the material thereby permitting measurement of the scattering parameters of the material when an electromagnetic field is transmitted from said first connector port and received by said first connector port from which the electrical properties of the material can be computed.

2. The device in accordance with claim 1, wherein the electromagnetic field is transmitted from said first connector port is received by said second connector port from which the electrical properties of the material can be computed.

3. The device in accordance with claim 2, said device further comprising at least two shorting screws, each of said shorting screws retractable to and from each of said conduits wherein said shorting screws are capable of selectively retracting to short said conduits for calibration of said device.

4. The device in accordance with claim 3, wherein said device is Navy brass.

5. The device in accordance with claim 1, said device further comprising at least two shorting screws, each of said shorting screws retractable to and from each of said conduits wherein said shorting screws are capable of selectively retracting to short said conduits for calibration of said device.

6. The device in accordance with claim 5, wherein said device is Navy brass.

* * * * *